(12) United States Patent
Terstappen

(10) Patent No.: US 6,228,624 B1
(45) Date of Patent: May 8, 2001

(54) METHOD TO SELECT AND TRANSFECT CELL SUBPOPULATIONS

(75) Inventor: Leon W. M. M. Terstappen, Huntingdon Valley, PA (US)

(73) Assignee: Immunivest Corporation, Wilmington, DE (US)

( * ) Notice: Subject to any disclaimer, the term of this patent is extended or adjusted under 35 U.S.C. 154(b) by 0 days.

(21) Appl. No.: 09/230,394
(22) PCT Filed: Jul. 31, 1997
(86) PCT No.: PCT/US97/13523
§ 371 Date: Jan. 27, 1999
§ 102(e) Date: Jan. 27, 1999
(87) PCT Pub. No.: WO98/05791
PCT Pub. Date: Feb. 12, 1998

Related U.S. Application Data

(60) Provisional application No. 60/023,063, filed on Aug. 2, 1996.

(51) Int. Cl.[7] .................................................. C12N 15/87
(52) U.S. Cl. ........................................ 435/173.9; 435/459
(58) Field of Search ................................ 242/450, 489; 435/6, 173.1, 173.9, 325, 375, 455, 458, 459, 470; 514/44

(56) References Cited

U.S. PATENT DOCUMENTS 5,460,831   10/1995   Kossovsky et al. .

FOREIGN PATENT DOCUMENTS 9423738   10/1994   (WO) .

OTHER PUBLICATIONS

R. Padmanabhan et al., "Purification of Transiently Transfected Cells by Magnetic Affinity Cell Sorting", Analytical Biochemistry, 170: 341–348 (1988).

M. Pilon et al., "Transient Expression of the CD2 Cell Surface Antigen as a Sortable Marker to Monitor High Frequency Transfection of Human Primary B Cells", The Journal of Immunology, 146: 1047–1051 (1991).

T. Giordano et al., "Isolation of a Population of Transiently Transfected Quiescent and Senescent Cells by Magnetic Affinity Cell Sorting", Experimental Cell Research, 192: 193–197 (1991).

Primary Examiner—Robert A. Schwartzman
Assistant Examiner—Thomas G. Larson
(74) Attorney, Agent, or Firm—Dan Dorfman Harrell and Skillman, P.C.

(57) ABSTRACT

A method for transfecting and separating cells is disclosed. The method comprises preparing magnetic particles coated with genetic material and a cell-specific ligand, and using the particles to transfect target cells. The target cells may then be separated from the non-target cells by using a magnetic field.

1 Claim, 1 Drawing Sheet

METHOD TO SELECT AND TRANSFECT CELL SUBPOPULATIONS

This application is the national stage of International Application No. PCT/US97/13523, which claims the benefit of U.S. Provisional Application No. 60/023,063, filed Aug. 2, 1996.

BACKGROUND OF THE INVENTION

The infection or transfection of cells by infectious viruses or retroviruses has been known for many years. Many methods for improving the rate of transfection have been used. Calcium chloride treatment of the cells has been used to allow naked DNA to pass through the cellular membrane. Improved vectors have been developed for increasing the level of infection. The use of lipids or liposomes to deliver the genetic material have also been used with some amount of success.

Particle mediated delivery has been used to transform numerous types of cells with a gold microparticle mediated delivery of DNA. The technique has been described in numerous publications and has advanced enough to merit a product which has been marketed by BioRad under the name Biolistic PDS. The use of this and similar systems are described in U.S. Pat. Nos. 4,945,050; 5,015,580; and 5,120,657 and international patent applications WO 95/29703 and WO 93/17706. An improvement upon the particle mediated delivery was made by Palsson, as disclosed in U.S. Pat. No. 5,534,423. The Palsson method includes loading a vector and the cells to be transformed into a centrifuge apparatus and spinning it to bring the vectors into contact with the cells. A spinnable disk and an electrolytic system are also envisioned.

SUMMARY OF THE INVENTION

The instant invention provides a method for transfection of target cells by which the transfection efficiency of vectors and target cells is improved by bringing the target cell and the vector in contact. This is achieved by immobilization of both the vector containing the relevant genetic material and the ligand specific for the target cells on a particle. When such particle is now incubated with a test sample consisting of a cell mixture containing the target cells, the ligand specific for the target cells will bind to the target cells and thus bring the vector in contact with the target cells. The target cells can now be separated from the non target cells by isolation of the particle-cell construct, thus achieving both enrichment of target cells and transfection of the target cells.

DETAILED DESCRIPTION OF THE INVENTION

Figure 1:
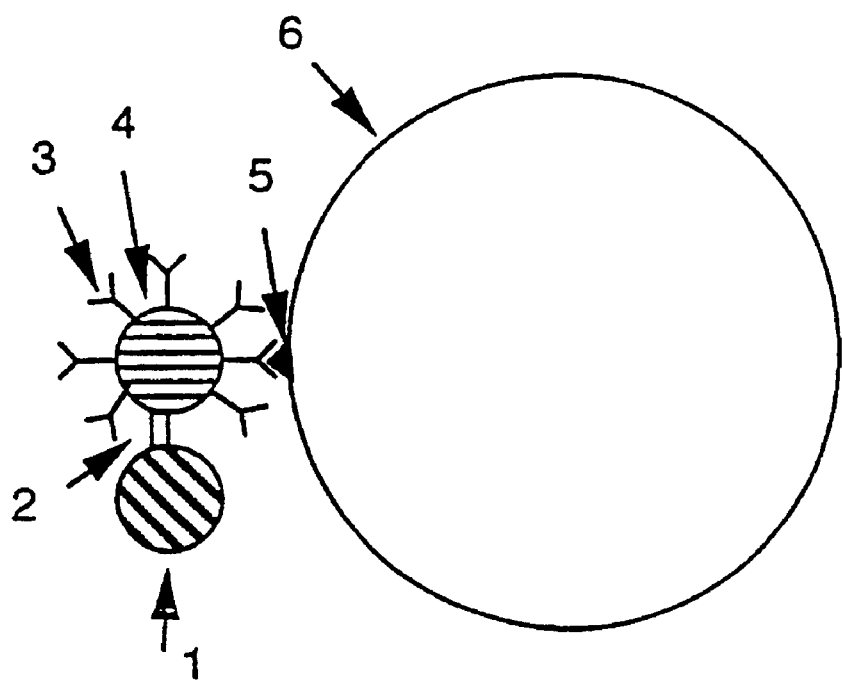
FIG. 1 is a schematic diagram of the separation and transfection of a target cell with a particle associated with a vector.

As used herein, the term "transfection" means the introduction of DNA, RNA, other genetic material, protein or organelle into a target cell.

As used herein, the term "vector" means any particle capable of transfecting a target cell. Vectors known to the art include, for example, viruses, spheroplasts or liposomes containing genes, and free nucleic acids containing genes, such as plasmids or nucleic acid fragments. Viruses useful in the methods of this invention include retroviruses (such as murine amphotropic virus), baculovirus, SV40-type viruses, polyoma viruses, adenoviruses, Epstein-Barr viruses, herpes simplex virus, vaccinia viruses and papilloma viruses. One can readily employ other vectors not named but known to the art. The methods of this invention are particularly useful for increasing rates of infection by vectors having half-lives of less than 24 hours, such as the murine amphotropic virus and baculovirus. However, they are also useful for increasing rates of infection for vectors having longer half-lives. Adsorption of vectors by cells depends, in part, on concentration of the vector in solution. By imparting directed motion to the vectors in the direction of the cells, the methods of this invention effectively increase the concentration of the vectors in the vicinity of the cells, resulting in more adsorption and infection.

As used herein, the term "target cell" refers to cells capable of being infected by a vector. Target cells may originate from any unicellular organism, plant, or animal, and include those cells of human origin. Cells useful for gene therapy are particularly useful in this invention. They include, for example, bone marrow cells, lymphocytes, fibroblasts, keratinocytes, hepatocytes, endothelial cells, neurons, muscle cells, epithelial cells, hematopoietic stem cells. This invention further contemplates use of cells taken from a patient or subject with the intent of infecting those cells and re-introducing them into the patient or subject.

As used herein, the term "particle" refers to any solid micro-particle with a diameter between 30 nm to 5 microns. These particles may be made of any type of natural or synthetic material and are optionally coated with a natural or synthetic polymer. Microparticles of the invention include polystyrene, latex, and metal oxides. Preferred are particles between the sizes of about 3 nm and 200 nm. Particularly preferred are magnetic microparticles particles between the sizes of about 30 nm and 200 nm.

The term "magnetic microparticle" refers to a material which may or may not be permanently magnetic, which also may be paramagnetic or super-paramagnetic but which in all cases exhibits a response in a magnetic field, i.e., is magnetically responsive. Many techniques have been suggested in the prior art for the preparation of such magnetic particles or organo-magnetic materials, including U.S. Pat. Nos. 5,512,332; 4,795,698; 4,230,685; 3,970,518; 4,554,088; 3,970,518 and 4,018,886. European patent number 0 489 119 also teaches the preparation of resuspendable coated particles.

The magnetic particles of the current invention are preferably between the sizes of 30 nm and 200 nm and are optionally coated with a natural or synthetic polymer. Associated with this magnetic particle is the vector used to transfect the cell of interest. The magnetic particles could be coated with or specifically linked to DNA, RNA, a virus, a retrovirus, a prion, or other infectious material as described above. Also associated with the magnetic particle is an immunospecific ligand. The ligand can be linked through a covalent or non-covalent bond to a functionality on the surface of the magnetic particle, or the ligand may be used to coat the particle. In one embodiment, the ligand coated magnetic particle and the vector associated magnetic particle are not the same.

One embodiment of the instant invention is schematically represented by FIG. 1. In FIG. 1, the target cell 6 will be approx. 5–50 mm in diameter. Receptor 5 is located on the surface of the target cell and specifically interacts with immunospecific ligand 3, which is coated upon particle 4, which has a diameter of 30–200 nm. Also associated with particle 4 through bond 2 is vector 1, which will have a size of approx. 1–100 nm. In this FIGURE, the target cell and the particle associated with the vector have already been brought into contact, allowing the immunospecific ligand 3 to react with the receptor 5 on the surface of the target cell 6, thus forming a particle-cell construct. Upon incubation of the particle cell construct under the appropriate conditions of temperature and culture media, infection of the target cell by the vector should result in the transfer of genetic material to the cell and thus to transfection of the target cell. Optionally, bond 2 may be broken after formation of the particle-cell construct to further facilitate infection of the target cell by the vector, for example, using the release techniques described in commonly owned, co-pending U.S. application Ser. No. 08/395,967, the entire disclosure of which is incorporated by referenced herein.

When desired, isolation of the particle-cell construct could be through the use of a column, coated surface, or any other means of particle manipulation known in the art. The method of the instant invention brings the target cell and the vector desired to transfect said cell into close proximity, thus improving the chances that the vector will in fact transfect the target cell. In other words, the local concentration of vector and target cell are increased.

In a preferred embodiment, a magnetic microparticle is coated with immunospecific ligand and associated with a vector. Once the target cell and the magnetic particle have been brought into contact, a magnetically responsive cell construct is formed. When this cell construct comes under the influence of a magnetic field gradient, either by the placement of the test sample containing the cell construct into a magnetic device, the generation of a magnetic field in the container which holds the test sample or the flowing of the test sample through a flow-through device, one section of which includes a magnetic field gradient, the cell construct will respond to the field gradient, moving to the region of highest field, thus separating from the remainder of the test sample. Optionally, the remaining test sample which is not magnetically responsive can be removed. This magnetic embodiment of the instant invention provides for the separation of the target cell from the test sample, thus limiting the amount of manipulation necessary in the transfection protocol, which will further increase cell viability and therefore transfection efficiency.

Although FIG. 1 depicts the direct specific interaction of ligand 3 with receptor 5, it should be apparent to one skilled in the art, that an indirect specific interaction is also possible. For example a biotinylated monoclonal antibody which is specific to the cell surface receptor may be incubated with the test sample which contains the target cell. In this embodiment a magnetic particle coated with avidin or streptavidin could be used to select the target cell. It should also be obvious to one skilled in the art that any type of ligand would be useful in order to practice the teaching of the instant invention. For example, a monoclonal antibody would provide a specific interaction with the cell, but also envisioned is the use of single chain antibodies, polypeptides selected from a library of peptides, or polyclonal antibodies.

In another embodiment of the instant invention, a plurality of magnetic particles are employed. One set of magnetic particles can be coated with ligand which specifically interacts with the target cell, either directly or indirectly, as described above. A second set of magnetic particles may be associated with the vector containing the genetic material to transfect the cell. After incubation of the test sample with the ligand-coated magnetic particles, the vector-associated magnetic particles could be added and the magnetic field gradient generated. Upon generation of the field gradient in the test sample, the target cell and the vector would come into close proximity and the opportunity for the vector to transfect the cell would be increased. Optionally, the vector-associated magnetic particles could be added to the target cells after said cells had been collected under the influence of the magnetic field gradient. When the vector associated magnetic particles come into the field gradient, they will accelerate toward the target cell, increasing the probability of transfection.

EXAMPLE

Enrichment and Transfection of Hematopoietic Progenitor Cells

Gene transfer technologies are of interest in view of their potential to correct a large variety of somatic cell defects or to make the transduced cells resistant to treatments which are otherwise detrimental for these cells. A procedure commonly used to enrich for hematopoietic progenitor cells is to select cells expressing the CD34 antigen from bone marrow or peripheral blood. This is for example achieved by immobilization of monoclonal antibodies specific for CD34 on magnetic particles. After incubation of the cell suspension with the immunomagnetic particles, the cell suspension is placed in or passed through a magnetic separator and the cells labeled with immunomagnetic particles are separated from the cell mixture. The CD34+ enriched cells are then exposed to supernatants containing for instance retroviral vectors. This transfection process is inefficient and generally results in a low percentage of transfected target cells. A means to increase this efficiency is to increase the movement of the particles towards the target cells such that the random Brownian motion is overcome. In the present invention the movement of the vector towards the target cell is achieved by immobilizing both the vector (retrovirus containing the genetic information) and the ligand (anti-CD34) on a magnetic particle. After an incubation period of a bodily fluid containing the target cells with the anti-CD34 and retrovirus labeled magnetic particle, the fluid is exposed to a magnetic field. The target cells labeled with the magnetic particles are then concentrated at the surface with the highest magnetic gradient which further increases the specific contact between target cells and vectors. The target cells are thus separated from the heterogeneous mixture and simultaneously brought in contact with the retrovirus permitting a more efficient transfection.

I claim:

1. A method for transfecting a target cell with DNA and magnetically selecting the resulting cell from a test sample, comprising the steps of:

providing magnetic particles coated with a ligand which specifically binds, either directly or indirectly, to said target cell, said magnetic particles being associated with a vector containing said DNA;

contacting a test sample containing said target cell with said magnetic particles under conditions forming a magnetically responsive particle-cell complex and effecting transfection of said target cell with said DNA via said vector; and generating in the test sample a magnetic field gradient of sufficiently high intensity to separate magnetically the transfected target cells from said test sample.

* * * * *